United States Patent [19]

Noonan, Jr.

[11] Patent Number: 4,915,700

[45] Date of Patent: Apr. 10, 1990

[54] SYRINGE

[76] Inventor: Thomas J. Noonan, Jr., 779 Southbridge St., Auburn, Mass. 01501

[21] Appl. No.: 221,294

[22] Filed: Jul. 19, 1988

[51] Int. Cl.⁴ .............................................. A61M 5/32
[52] U.S. Cl. .................................... 604/195; 604/110
[58] Field of Search ............... 604/195, 194, 196, 198, 604/192, 110, 228

[56] References Cited

U.S. PATENT DOCUMENTS 4,507,117  3/1985  Vining et al. ..................... 604/196
4,804,370  2/1989  Haber et al. ..................... 604/195
4,813,936  3/1989  Schroeder ......................... 604/195
4,826,484  5/1989  Haber et al. ..................... 604/195

FOREIGN PATENT DOCUMENTS 476501  9/1969  Switzerland ....................... 604/195

Primary Examiner—Stephen C. Pellegrino
Attorney, Agent, or Firm—Norman S. Blodgett; Gerry A. Blodgett

[57] ABSTRACT

A single use syringe in which the needle is rendered inoperative by retraction after injection has taken place.

6 Claims, 1 Drawing Sheet

SYRINGE

BACKGROUND OF THE INVENTION

It has been very well established that many diseases are spread by persons who share intravenous needles. Persons who share needles in this way are usually drug addicts and this brings about the spreading of such diseases as AIDS or Hepatitis. It has been suggested, therefore, that the disease spread can be reduced by making clean needles available to drug users. However, there is no way of controlling the multiple use of needles when this is done. In addition, there is a rising concern among medical personnel who are involved in hypodermic needle use, either in connection with injection of medicines or in taking blood samples. A needle which has been used for this purpose, if contaminated with the disease, is a very dangerous instrumentality; there is documented evidence that nurses and doctors scratched by accident with such needles have had disease and even death from the contact. These problems have been obviated in a novel manner by the present invention.

It is therefore, an outstanding object of the invention to provide a syringe that includes a mechanism that would allow a only one loading into the syringe cylinder of any particular drug or fluid that is to be injected.

Another object of this invention is the provision of a hypodermic syringe having a mechanism that causes the plunger and needle assembly to become an integral assembly, thus preventing a second loading of the drug or fluid, because the mechanism stops the pump suction ability of the entire product.

A further object of the present invention is the provision of a hypodermic syringe that will assist in the national and international efforts to inhibit the spread of the AIDS virus among those intravenous drug users who now tend to share needles with fellow drug users.

It is another object of the instant invention to provide a hypodermic needle that is capable of only one use, thus preventing the spread of any one of a number of diseases brought about by the sharing of contaminated needles.

A still further object of the invention is the provision of a hypodermic needle that, after a first use, causes the needle to be retracted into the cylinder, thus providing for safer disposal and for relief of the significant level of fear among health car workers who must daily work with hypodermic syringes.

It is a further object of the invention to provide a hypodermic syringe which is simple in construction, which can be manufactured from relatively inexpensive materials, and which is capable of use and storage with a minimum of care.

With these and other objects in view, as will be apparent to those skilled in the art, the invention resides in the combination of parts set forth in the specification and covered by the claims appended hereto.

SUMMARY OF THE INVENTION

In general, the invention consists of a hypodermic syringe having an elongated cylinder with a first bore extending into one end and terminating in a closure at the other en. A second bore extends through the closure coaxially of the first bore. A plunger lies slidably in the first bore and has a section at the inner end fitting tightly in the bore while having a section at the outer end extending from the plunger for use in sliding the plunger to and from in the bore. A needle assembly is provided, having a main body that sits snugly and slidably in the second bore and having a flange that fits snugly and slidably in the first bore. A detent means is associated with the needle assembly to lock the needle assembly to the plunger when the plunger has been initially completely depressed, so that the needle assembly is caused to retract into the cylinder when the plunger is subsequently retracted.

More specifically, the plunger has a coaxial passage extending entirely through it and the needle assembly has a rod that fits slidably in the passage. The detent means consists of cooperating parts of the plunger and the free end of the rod. The free end of the rod is provided with spaced, parallel fingers, each of which is provided with an outwardly-extending abutment, while the passage in the plunger is provided with a shoulder that cooperate with the finger abutments as the plunger approaches the completely depressed condition and retraction begins.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
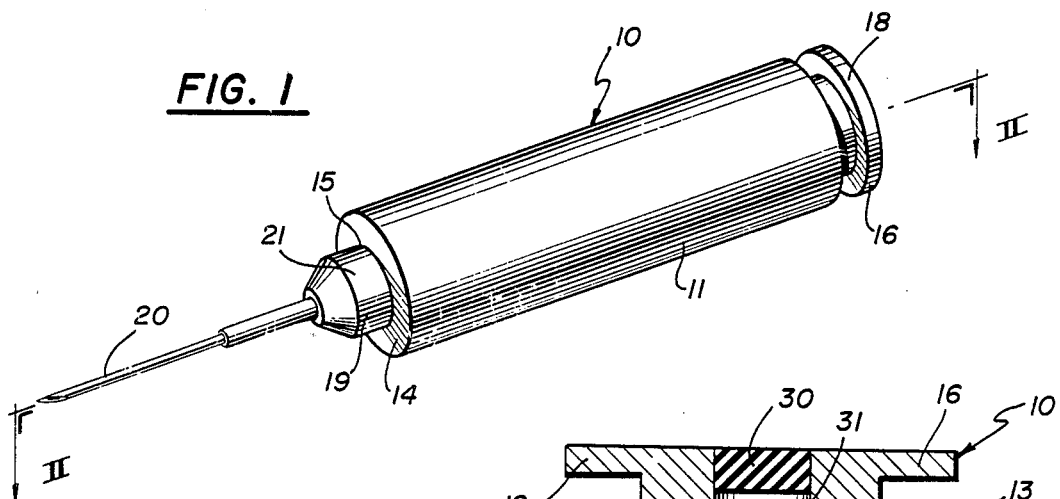
FIG. 1 is a perspective view of a hypodermic syringe incorporating the principles of the present invention.

Referring first to FIG. 1 wherein are best shown the general features of the invention, it can be seen that the hypodermic syringe, indicated generally by the reference numeral 10, is shown as having an elongated cylinder 11 having a closure 14 at one end. A plunger 16 extends into the cylinder and a needle assembly 19 extends through a bore 15 through the closure 14 and carries a hypodermic needle 20. The plunger 16 is provided with a section 18 in the form of a flange permitting the plunger to be withdrawn, retracted, or depressed.

Figure 2:
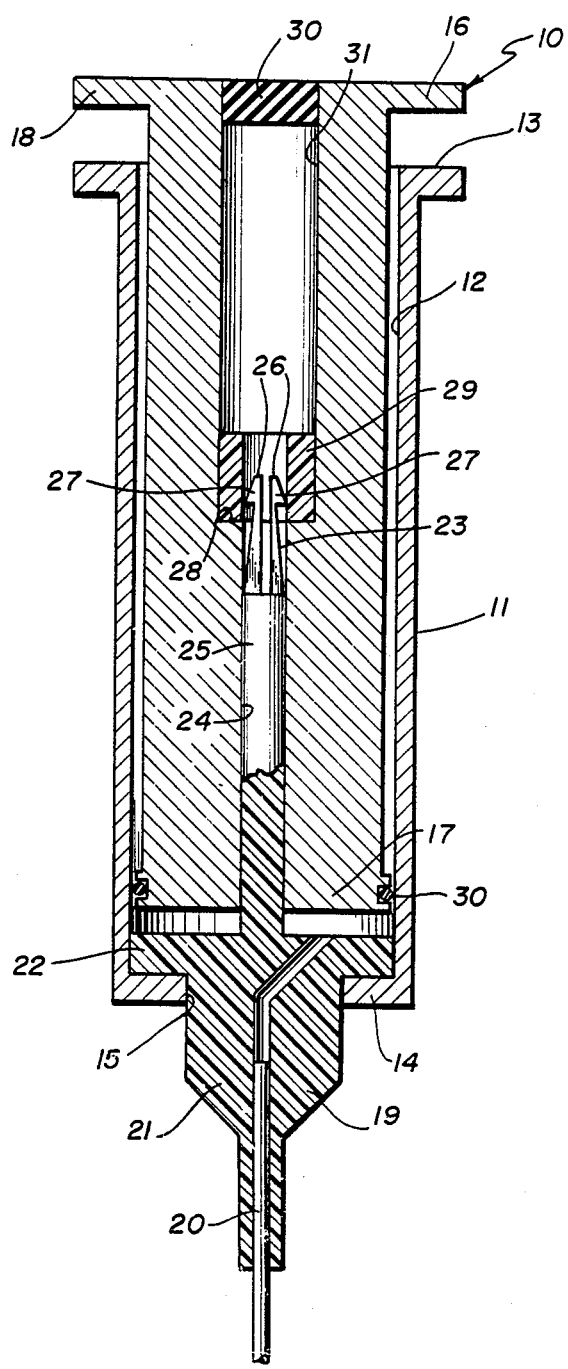
FIG. 2 is a vertical sectional view of the syringe taken along the line II—II of FIG. 1.

Referring now to FIG. 2, it can be seen that the cylinder 11 is provided with a first bore 12 which extends into one end 13 of the cylinder. The first bore terminates at the other end at the enclosure 14 and a second bore 15 extends through the closure coaxially of the first bore 12.

The plunger 16 lies and extends through the first bore 12 and has a section 17 fitting tightly in the bore; this section carries a rubber O-ring or seal 30. As has been stated above, a section 18 in the form of a flange at the other end of the plunger is provided for use in manually sliding the plunger to and from in the bore 12.

The needle assembly 19 includes a main body 21 which fits snugly and slidably in the second bore 15. The needle assembly is also provided with a flange 22 that fits snugly and slidably in the first bore 12.

Detent means 23 is associated with the needle assembly to lock the needle assembly to the plunger when the plunger has been initially completely depressed, so that the needle assembly is caused to retract into the cylinder when the plunger is subsequently retracted.

As is evident in FIG. 2, the plunger 16 has a coaxial passage 24 in the form of a bore which extends entirely through the plunger and whose outer end is closed by a plug 30 which is cemented in place. The needle assembly 19 is provided with a rod 25 which fits slidably in the passage. The detent means 23 consists of cooperating parts of the plunger and the free end of the rod 25. More specifically, the free end of the rod 25 is provided with a pair of spaced parallel fingers 26 each of which is provided an outwardly-extending abutment 27. The passage 24 in the plunger is provided with a shoulder 28 formed by a counterbore 31. This shoulder cooperates with the finger abutments 27 as the plunger reaches the completely depressed condition and retraction begins.

A sleeve 29 is slidable in the counterbore 31 and is provided to maintain the abutments 27 out of engagement with the shoulder 28 during an initial filling retraction of the plunger. This sleeve becomes inoperative during the depression movement of the plunger, so that, when the plunger is subsequently retracted, the abutments 27 engage the shoulder 28 and the needle assembly 19 is drawn entirely into the cylinder along with the needle 20.

The operation and the advantages of the present invention will now be readily understood in view of the above description. In order to fill the hypodermic syringe 10 with the fluid which is to be intravenously injected, the cylinder 11 is held in one hand and the other hand is used in conjunction with the section 18 of the plunger to pull the plunger outwardly of the first bore 12. This causes a vacuum to develop between the seal 30 and the flange 22 of the needle assembly 19. As the plunger is further withdrawn, the fluid flows into and fills the cylinder; when the plunger reaches its extreme position outwardly, the syringe is ready for the injection of the fluid. It should be noted that, as the plunger is retracted, there is no engagement between the abutments 27 on the rod 25 of the needle assembly with the shoulder 28, because of the presence of the sleeve 29 which, because of the friction between the abutments and the inner surface of the sleeve, causes the sleeve to be forced downwardly against the shoulder 28. After the needle 20 has been introduced into the vein of the person being treated, the plunger 16 is then pressed inwardly causing it to move into the first bore 12 and express the fluid. The friction between the abutments 27 of the rod 25 at that time and the inner surface of the sleeve 29 are such as to press the sleeve 29 along the counter bore 31. By the time the plunger reaches the position in which most of the fluid has been introduced into the patient, the sleeve 29 lies well away from the shoulders 28. Then, when one attempts to retract the plunger 16 for a reload or deliberately in order to render the syringe inoperative, the fingers 26 snap outwardly and the shoulders on the abutments 27 engage the shoulder 28 on the plunger. Therefore, as the plunger proceeds outwardly of the first bore 12, the needle assembly is carried with it. It moves smoothly through the first bore along with the plunger and eventually the needle 20 lies entirely inside of the cylinder.

It can be seen, then, that, when the needle is used in this way, two things happen. If the medical person wishes to render the needle inaccessible, so that it cannot accidentally scratch a nurse or doctor, the plunger is pulled completely out, causing the needle to retract inside the cylinder. In the finished condition, of course, the sleeve 29 is removed away from the fingers 26 and lies nearer to the entrance of the counterbore 31. If one pushes the plunger 16 inwardly again, the plunger simply causes the needle assembly to slide back out again, but any attempt to retract the plunger to introduce fluid into the cylinder will simply cause the needle to retract again. In other words, in the case of medical personnel, they will probably discard the package with the needle assembly entirely inside the cylinder. If one attempts to abuse the situation by presenting the needle back into operative condition again, the retraction of the plunger will not cause fluid to enter syringe for use by a drug addict for instance, but will only cause repeated retraction of the needle assembly to the inside of the cylinder. In other words, the syringe is rendered useless in either situation.

The present invention, when incorporated into a hypodermic syringe, will allow only a single loading into the syringe cylinder of any particular drug or fluid that is to be injected. After injection, the mechanism causes the plunger and the needle assembly to become an integral assembly, thus preventing a second loading of a drug or fluid, since the mechanism stops the pump suction ability of the entire product. The value of this invention is such that it will assist in the national and international efforts to inhibit the spread of the AIDS virus among intravenous drug users who now tend to share needles with fellow drug users. The spread of any one of a number of diseases, such as AIDS or hepatitis is brought about by this sharing of a contaminated needle. It has been determined that in the calendar year 1987, an estimated 12,000–15,000 health care workers in the United States contracted the Hepatitis-B virus by accidentally sticking themselves with contaminated needles. Of this 12,000–15,000 estimate, 200–300 resulted in fatality.

The present invention, in addition to preventing a second injection, also allows the needle to be retracted back up and into the cylinder, thus allowing for considerably safer disposal and relief of the significant level of fear amongst health care workers who must daily work with hypodermic syringes. It has been noticed that the widespread fear of this contamination has been evidenced by the number of nurses, blood sample technicians, and dentists who are now leaving or seriously restricting their professions.

The invention having thus been described, what is claimed as new and desired to secure by Letters Patent is:

1. Syringe comprising:
  (a) an elongated cylinder having a first bore extending into one end and terminating in a closure at the other end, a second bore extending through the closure coaxially of the first bore,
  (b) a plunger extends through the first bore and has a section fitting tightly in the bore, while having a section extending from the said first end for use in sliding the plunger to and from in the bore,
  (c) a needle assembly having a main body that fits snugly and slidably in the second bore and has a flange that fits snugly and slidably in the first bore, the plunger having a passage extending therethrough and the needle assembly having a rod fitting slidably in the passage, and
  (d) detent means is associated with the needle assembly to lock the needle assembly to the plunger when the plunger has been initially completely depressed, so that the needle assembly is caused to retract into the cylinder when the plunger is subsequently retracted.

2. Syringe as recited in claim 1, wherein the plunger has a coaxial passage extending entirely through it and the needle assembly has a rod that fits slidably in the passage.

3. Syringe as recited in claim 2, wherein the detent means consists of cooperating parts of the plunger and the free end of the rod.

4. Syringe as recited in claim 3, wherein the said free end of the rod is provided with a pair of spaced, parallel fingers each of which is provided with an outwardly-extending abutment, and wherein the passage in the plunger has a counterbore defining a shoulder that cooperate with the finger abutments as the plunger approaches the completely depressed condition and retraction begins.

5. Syringe as recited in claim 4, wherein a sleeve is provided slidable to counterbore to maintain the abutments out of engagement with the shoulder during an initial filling retraction of the plunger, which sleeve becomes inoperative during the depression movement of the plunger, so that, when the plunger subsequently is retracted, the abutments engage the shoulder and the needle assembly is drawn entirely into the cylinder.

6. Syringe comprising:

(a) an elongated cylinder having a first bore extending into one end and terminating in a closure at the other end, a second bore extending through the closure coaxially of the first bore, (b) a plunger extends through the first bore and has a section fitting tightly in the bore, while having a section extending from the said first end for use in sliding the plunger to and from in the bore, (c) a needle assembly having a main body that fits snugly and slidably in the second bore and has a flange that fits snugly and slidably in the first bore, the plunger having a passage extending therethrough and the needle assembly having a rod fitting slidable in the passage, (d) detent means is associated with the needle assembly to lock the needle assembly to the plunger when the plunger has been initially completely depressed, so that the needle assembly is caused to retract into the cylinder when the plunger is once subsequently retracted, and (e) means causing the needle assembly to remain in the cylinder when the plunger is moved in and out after it has once been so retracted.

* * * * *